United States Patent
He et al.

(10) Patent No.: US 7,848,489 B1
(45) Date of Patent: Dec. 7, 2010

(54) X-RAY DIFFRACTOMETER HAVING CO-EXITING STAGES OPTIMIZED FOR SINGLE CRYSTAL AND BULK DIFFRACTION

(75) Inventors: Bob B. He, Madison, WI (US); Gerald T. Schwarz, Madison, WI (US)

(73) Assignee: Broker AXS, Inc., Madison, WI (US)

( * ) Notice: Subject to any disclaimer, the term of this patent is extended or adjusted under 35 U.S.C. 154(b) by 65 days.

(21) Appl. No.: 12/417,032

(22) Filed: Apr. 2, 2009

(51) Int. Cl.
   *G01N 23/20* (2006.01)
   *G01N 23/207* (2006.01)
(52) U.S. Cl. ............... 378/79; 378/71; 378/81
(58) Field of Classification Search ............ 378/70–81
   See application file for complete search history.

(56) References Cited

U.S. PATENT DOCUMENTS

| | | | |
|---|---|---|---|
| 5,359,640 A | 10/1994 | Fink et al. | |
| 5,594,546 A * | 1/1997 | Westerfield et al. | 356/246 |
| 6,918,698 B2 * | 7/2005 | Nordmeyer et al. | 378/205 |
| 7,274,769 B2 * | 9/2007 | Nordmeyer et al. | 378/80 |
| 2002/0100309 A1 * | 8/2002 | Xu et al. | 72/462 |
| 2003/0012334 A1 * | 1/2003 | Kurtz et al. | 378/73 |
| 2005/0084066 A1 * | 4/2005 | Kim et al. | 378/79 |

OTHER PUBLICATIONS

3 Brochures on STADI-P, STADI-MP, and STADI-MP Combo diffractometers and Page on Stoe Company History, http://www.stoe.com.*
He, Bob, "Introduction to Two-Dimensional X-Ray Diffraction", Power Diffr., vol. 18, No. 2, pp. 71-85, Jun. 2003.
Katrusiak, Andrzey, "High-Pressure Crystallography", Acta Cryst. (2008). A64, pp. 135-148.
Dawson, Alice, et al., "Use of a CCD Diffractometer in Crystal Structure Determinations at High Pressure", J. Appl. Cryst. (2004). 37, pp. 410-416.
Massey, W., et al., "A Four-Circle Single Crystal Diffractometer With a Rotating Anode Source", J. Appl. Cyrst. (1976). 9, pp. 119-125.
* cited by examiner

*Primary Examiner*—Edward J Glick
*Assistant Examiner*—Anastasia Midkiff
(74) *Attorney, Agent, or Firm*—Law Offices of Paul E. Kudirka

(57) ABSTRACT

A diffractometer for X-ray diffraction measurements has two co-exiting sample stages which are mounted on the goniometer base simultaneously. A rotation stage is used for single crystal X-ray diffraction and an XYZ stage is used for general X-ray diffraction with bulky samples. The driving bases of both stages are located away from the instrument center so the measuring space in the vicinity of the instrument center is available to either of the two sample stages. With this arrangement, the rotation axis of the rotation stage stays aligned to the instrument center even when the XYZ stage is used for data collection. Therefore, realigning of the rotation stage to the instrument center is not necessary when switching the applications between the two stages.

12 Claims, 5 Drawing Sheets

X-RAY DIFFRACTOMETER HAVING CO-EXITING STAGES OPTIMIZED FOR SINGLE CRYSTAL AND BULK DIFFRACTION

BACKGROUND

X-ray diffraction is a non-destructive technique for the qualitative and quantitative analysis of crystalline material samples, which are generally provided in the form of single crystals or powders. In accordance with this technique, an X-ray beam is generated by an X-ray tube with a stationary anode, by a conventional rotating anode X-ray source or by a synchrotron source and directed toward the material sample under investigation.

When the X-ray beam strikes the sample, the X-rays produce Bragg angle reflections from the parallel and equally spaced atomic planes in the crystalline substance. Diffraction occurs if the path of the X-rays reflected by successive planes is a multiple of the X-ray wavelength. Therefore, the spacing between the atomic planes of a crystal can be determined by detecting the diffracted X-rays and measuring the first-order angles of diffraction. These measurements are usually performed by rotating the crystalline sample while taking diffraction measurements. The resulting pattern is called a diffractogram. Texture or crystal structure analysis can be performed on the sample by applying standard techniques to the series of diffractograms obtained from the sample.

A device called a "goniometer" is used to position and hold the various components of the X-ray diffraction system. The goniometer has multiple moveable arms or fixed dovetail mounts on which the X-ray source (or, for synchrotron sources, the X-ray optics), the sample and an X-ray detector are mounted. In order to acquire the diffraction data, the sample is typically rotated by a stepper or servo motor. FIG. 1 illustrates a typical diffractometer 100 used for diffraction measurements of a single crystal. The diffractometer 100 is built on a goniometer base 102 having stages 104 and 106 that rotate around two concentric main rotation axes $\omega$ and $2\theta$. The stage 104 rotating around the $2\theta$ rotation axis is used to support and position the detector 108 through the attached detector track 110. The x-ray source/optics 112 and collimator 114 is mounted on another track 116 attached to the goniometer base 102. The stage 106 rotating around the $\omega$ rotation axis is used to rotate the sample on the sample stage 118 relative to the incident X-ray beam from the collimator 114 and the detector 108. The sample stage 118 is the $\phi$ rotation stage which is used to rotate the single crystal sample. The $\phi$ rotation axis intersects the $\omega$ rotation axis at point C with a fixed angle $\chi$ between the two axes. The point C is referred to as the instrument center.

During a typical experiment, a single crystal sample 122 is mounted on the $\phi$ rotation axis by means of the goniometer head 120, which may additionally contain three orthogonal translation adjustments and/or tilt adjustments. The function of the goniometer head 120 is to bring the mounted single crystal sample 122 into the instrument center so that the incident X-ray beam through the collimator 114 strikes the sample 122 at the instrument center C and the sample stays in the instrument center while rotating about the $\phi$ axis and/or the $\omega$ axis. Some systems have a third sample rotation axis either as $\chi$ axis in Eulerian geometry or $\kappa$ axis in kappa geometry.

However, since most single crystal samples are very small in size, typically a few hundred microns to a millimeter, a diffractometer dedicated for single crystal X-ray diffraction such as that shown in FIG. 1 cannot handle a large bulky sample or multiple samples. In order to handle large or bulky samples, the diffractometer must have a different construction. FIG. 2 illustrates a typical diffractometer 200 used for general X-ray diffraction for large samples and multiple samples. The system is built on the same goniometer as the system shown in FIG. 1 and corresponding parts have been given corresponding numeral designations. The goniometer base 102 contains two concentric main rotating stages 104 and 106. The stage 104 rotates around the $2\theta$ rotation axis and supports and positions the detector 108 via the attached detector track 110. The x-ray source/optics 112 and collimator 114 are mounted on another track 116 attached to the goniometer base 102.

The stage 106 that rotates around the $\omega$ rotation axis is attached to the sample stage 206 via an arm 202 and rotates the stage 206 relative to the incident X-ray beam and detector. The XYZ stage 204 is used to hold large samples or multiple samples. The $\omega$ rotation axis intersects with the incident X-ray beam at the instrument center C and the XYZ stage 204 can bring a measuring spot on a large sample or multiple samples into the instrument center C. For certain experiments, the XYZ stage 204 may be replaced by a large Eulerian cradle with XYZ translations and rotations around the $\psi$ and $\phi$ axes in Eulerian geometry. Since this diffractometer is dedicated to handling large samples and multiple samples, it lacks a sufficient rotation range for single crystal diffraction.

Existing X-ray diffractometers are designed either for single crystal X-ray diffraction or general diffraction with powder samples, bulky samples or multiple samples. However in some X-ray diffraction laboratories, a diffractometer suitable for both single crystal diffraction and general diffraction may be necessary. One example is a diffraction system that will be used both for single crystals and for samples under high pressure in a diamond anvil cell (DAC). Due to the heavy weight and bulky size of the DAC, a motorized XYZ stage is necessary to hold and automatic align the sample. One solution is to replace the $\phi$ rotation stage 118 shown in FIG. 1 by the XYZ stage 204 shown in FIG. 2. However, reinstalling the $\phi$ rotation stage 118 and realigning the $\phi$ axis into the instrument center after each use of the XYZ stage 204 is a tedious job and may require a trained person with a set of special tools.

SUMMARY

In accordance with the principles of the invention, a diffractometer for X-ray diffraction measurements has two co-exiting sample stages which are mounted on the goniometer base simultaneously. A rotation stage is used for single crystal X-ray diffraction and an XYZ stage is used for general X-ray diffraction with bulky samples. The driving bases of both stages are located away from the instrument center so the measuring space in the vicinity of the instrument center is available to either of the two sample stages. With this arrangement, the rotation axis of the rotation stage stays aligned to the instrument center even when the XYZ stage is used for data collection. Therefore, realigning of the rotation stage to the instrument center is not necessary when switching the applications between the two stages.

DETAILED DESCRIPTION

Figure 1:
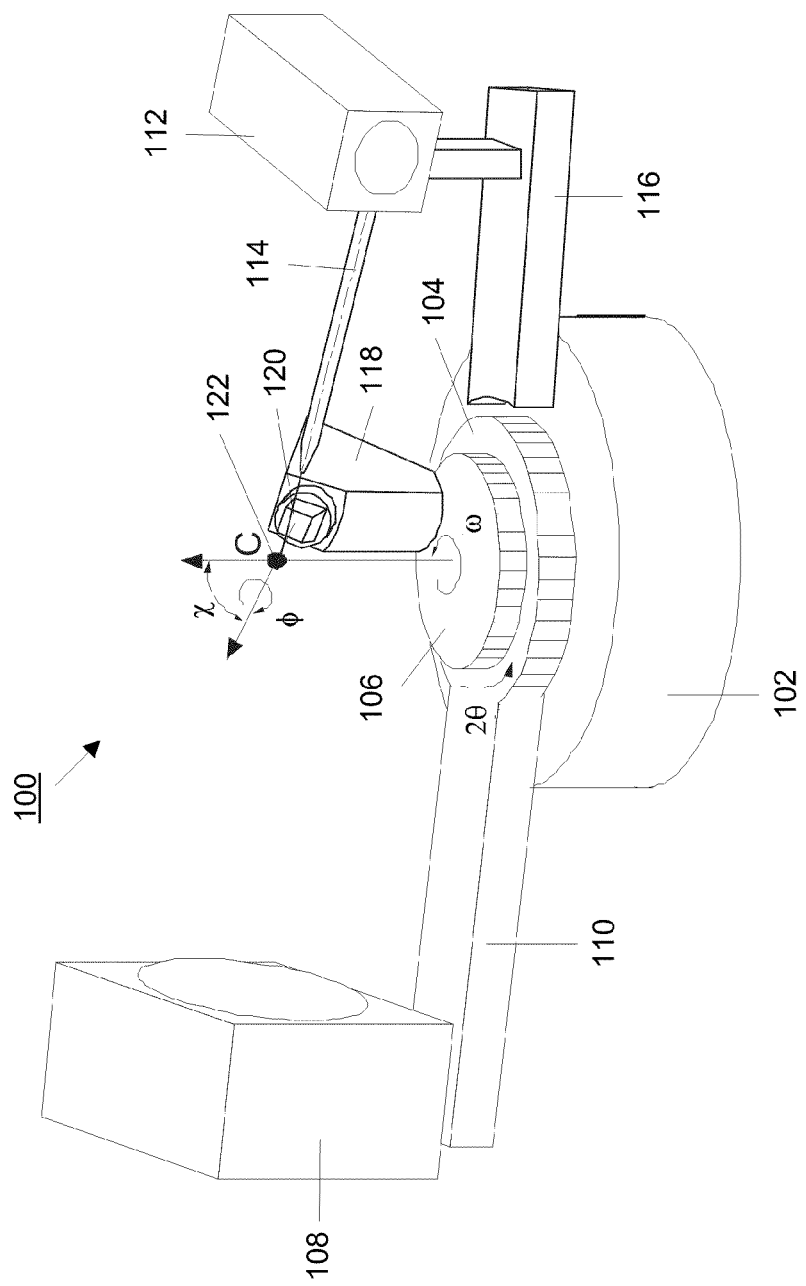
FIG. 1 is a perspective drawing of a conventional diffractometer with a configuration dedicated to single crystal diffraction experiments.
Figure 2:
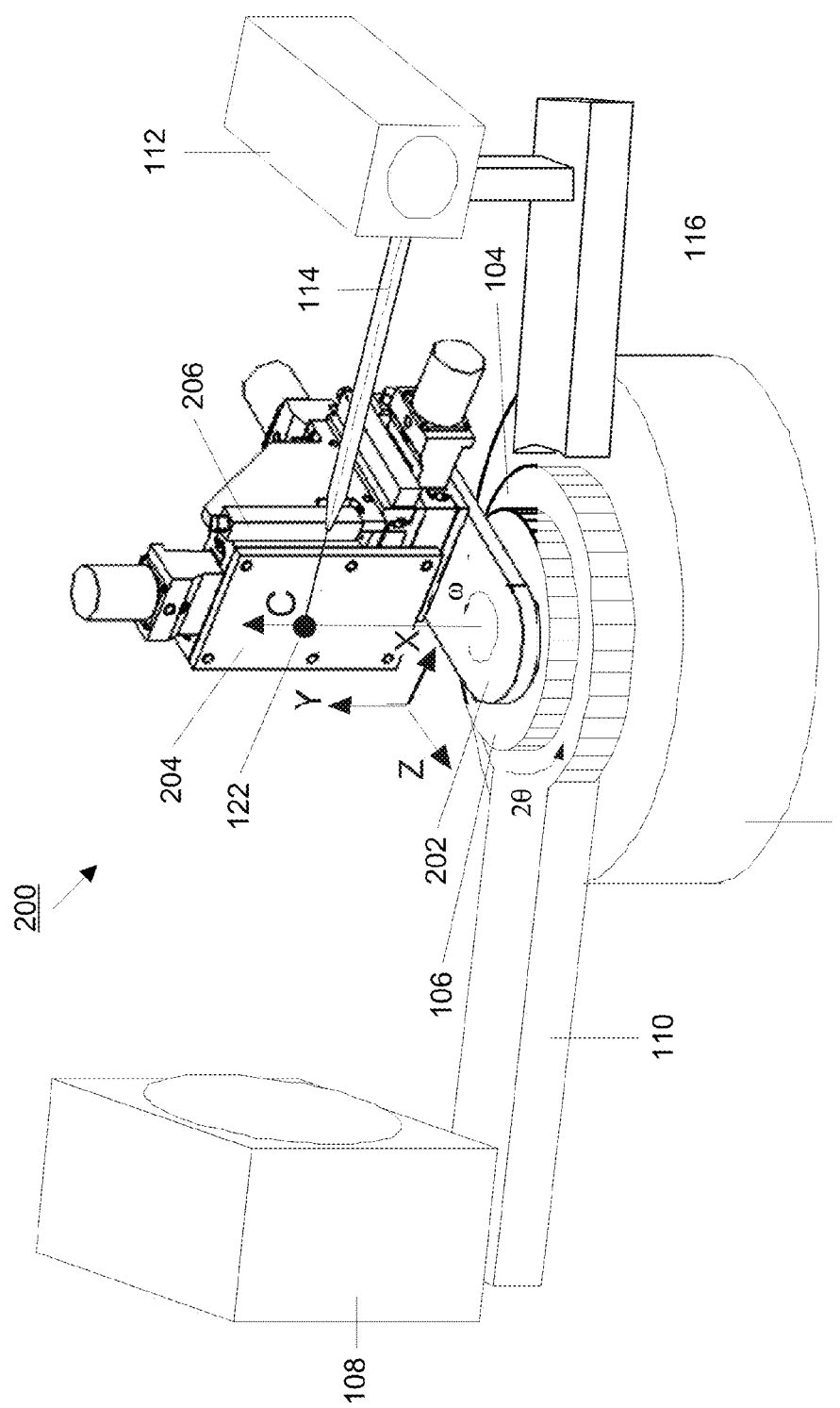
FIG. 2 is a perspective drawing of a conventional diffractometer with a configuration dedicated to general X-ray diffraction with bulky samples.
Figure 3:
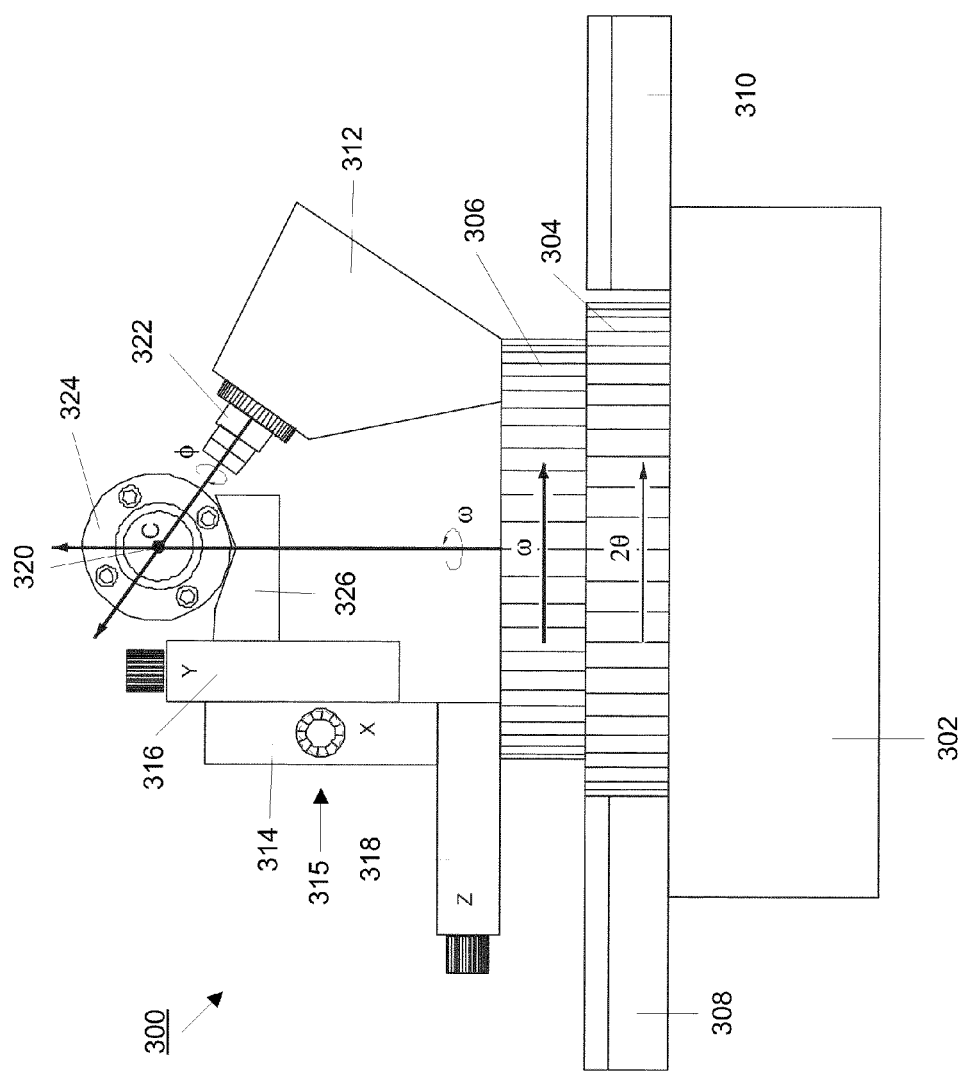
FIG. 3 is a plan view of a diffractometer with two co-exiting sample stages which are mounted on the goniometer base simultaneously in accordance with the principles of the invention.

FIG. 3 shows a plan view of a diffractometer 300 constructed in accordance with the principles of the invention. The system is built on a goniometer base 302 containing two concentric main rotating stages 304 and 306 that rotate around the 2θ and ω axes. The 2θ rotation axis stage 304 is used to support and position the detector (not shown) via the attached detector track 308. The x-ray source and optics (not shown) are mounted on another track 310 attached to the goniometer base 302. The ω rotation axis stage 306 is used to rotate the sample on a sample stage relative to the incident X-ray beam and detector.

In accordance with the principles of the invention, two sample stages 312 and 314-318 are attached to the ω axis stage 306. The sample stage 312 is a φ rotation stage which is used to rotate a single crystal sample. The φ rotation axis intersects the ω rotation axis at point C, which is the instrument center. The incident X-ray beam also strikes the sample at the instrument center. The single crystal sample 320 is mounted on the φ rotation axis via the goniometer head 322, which may also contain three orthogonal translation adjustments and/or tilt adjustments.

The sample 320 and goniometer head 322 can be detached from the φ rotation stage 312 when the system is used for X-ray diffraction with large samples. A large sample or multiple samples can be supported by the stage 315 having X, Y and Z moveable sections 314, 316 and 318, respectively. The XYZ stage 315 can move a spot of interest on a large sample into the instrument center for X-ray diffraction measurements. The stage 315 can also move several different spots on the sample into the instrument center sequentially for X-ray diffraction mapping, or can move several samples loaded on the XYZ stage 315 into the instrument center for X-ray diffraction data collection sequentially. The XYZ stage 315 can be either manually adjusted or motorized to reach all the positions.

As an example, as shown in FIG. 3, a diamond anvil cell (DAC) 324 is supported by a V-block 326 mounted on the Y portion 316 of the XYZ stage 315. A small DAC may be directly mounted on the φ rotation stage 312, but the φ rotation stage is designed for small single crystals. Therefore, a large DAC, a large sample or multiple samples would have to be supported by the XYZ stage 315.

The alignment of the sample into the instrument center by the XYZ stage 315 is aided by viewing the sample through a video microscope system (not shown). Since the XYZ stage 315 is mounted on the ω axis, the measuring spot on the sample stays in the instrument center with ω rotation. When not in use, the XYZ stage 315 can be driven to a position that yields a space for single crystal diffraction. Since there is no rotation axis on the XYZ stage 315, it is not necessary to align the XYZ stage 315 to the instrument center. Therefore, the XYZ stage 315 can either be left on the ω axis stage 306 or removed from the ω stage during the single crystal data collection with the φ stage. However, if a rotation axis is added to the XYZ stage 315, a pre-alignment of the stage becomes necessary if the stage is to be re-mounted to the ω axis after it has been removed from the ω axis.

Since both the φ stage 312 and the XYZ stage 315 are mounted on the same the ω stage 306 and the φ stage 312 is pre-aligned to the instrument center, a diffractometer equipped with such a combined stages can be used for either single crystal X-ray diffraction or general X-ray diffraction with large polycrystalline sample or multiple samples. Realignment of the diffractometer is not necessary when switching between the two applications.

Figure 4:
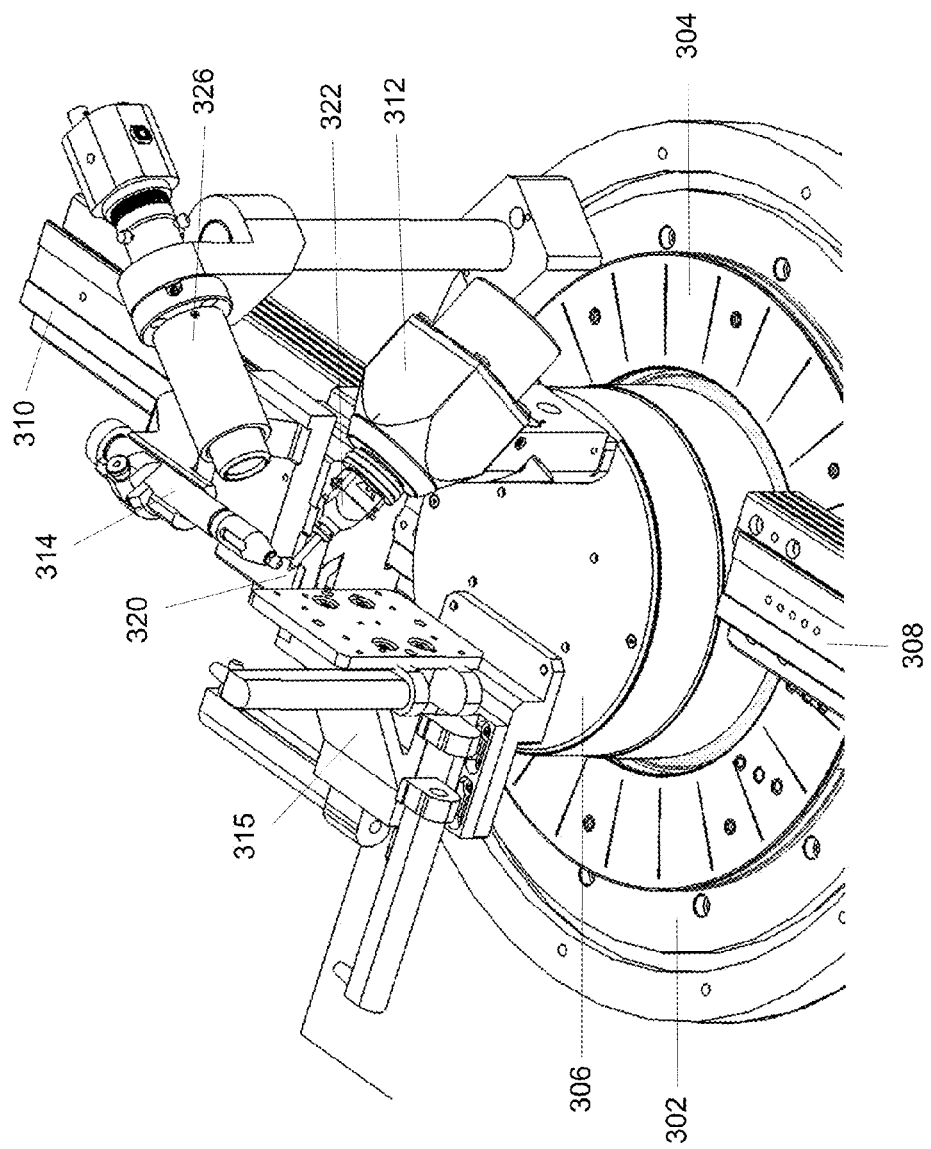
FIG. 4 is a perspective view of a diffractometer constructed in accordance with the principles of the invention which is configured for a single crystal diffraction experiment.

FIG. 4 is a perspective view of the inventive diffractometer in a configuration useful for single crystal diffraction. All the components have the same numeral designations as FIG. 3 except components not shown in FIG. 3, including the X-ray collimator 314 and the video microscope 326 which is used to align the sample to the instrument center. A single crystal sample 320 is loaded on the system. No sample is loaded on the XYZ stage 315

Figure 5:
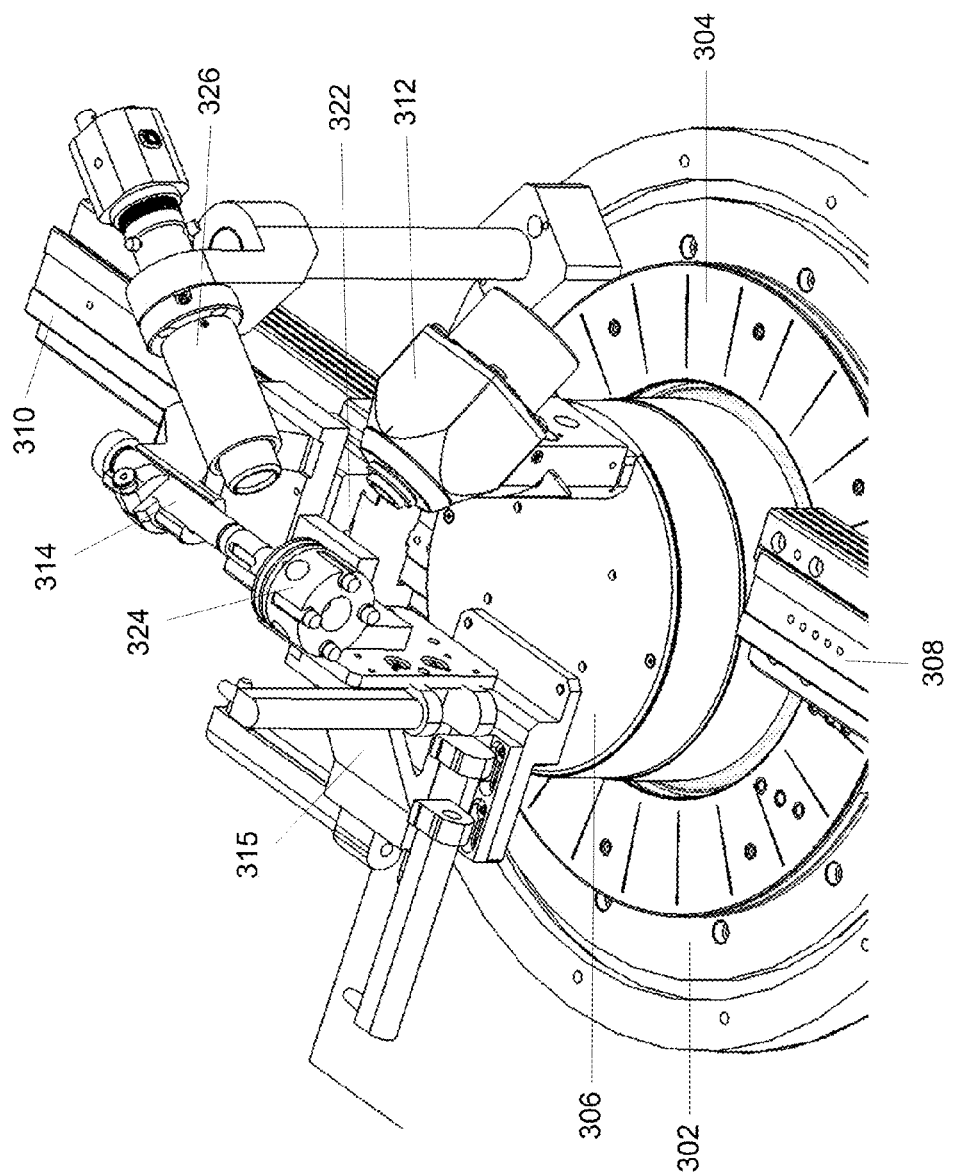
FIG. 5 is a perspective view of a diffractometer constructed in accordance with the principles of the invention which is configured for an X-ray diffraction experiment on a sample under high pressure in a DAC.

FIG. 5 is a perspective view of the inventive system configured for X-ray diffraction of a sample under high pressure in a DAC. As with FIG. 4, all the components are labeled with the same number as in FIG. 3. A DAC 324 is mounted on the XYZ stage 315. There is no goniometer head or single crystal sample mounted on the system.

While the invention has been shown and described with reference to a number of embodiments thereof, it will be recognized by those skilled in the art that various changes in form and detail may be made herein without departing from the spirit and scope of the invention as defined by the appended claims.

What is claimed is:

1. An X-ray diffractometer comprising:
   a base;
   a first stage that is attached to the base and rotates around an ω axis;
   a rotation stage that holds a crystal in a position suitable for a diffraction measurement and is mounted on the first stage at a first predetermined distance from the ω axis; and
   an XYZ stage that holds large and multiple samples in a position suitable for a diffraction measurement and is mounted on the first stage at a position diametrically opposed to the rotation stage and at a second predetermined distance from the ω axis, both the rotation stage and the XYZ stage being mounted on the first stage during an X-ray diffraction measurement.

2. The diffractometer of claim 1 having an instrument center located along the ω axis and wherein the first and second predetermined distances are sufficiently large to allow a crystal mounted on the rotation stage to be positioned at the instrument center without interference from the XYZ stage and to allow a sample mounted on the XYZ stage to be positioned at the instrument center without interference from the rotation stage.

3. The diffractometer of claim 1 wherein the rotation stage comprises a base mounted on the first stage and a goniometer head removably attached to the base in a manner that the goniometer head can be removed and reattached to the base without re-aligning the diffractometer.

4. The diffractometer of claim 3 wherein the base is mounted on the first stage in a position where the goniometer head can be removed and a diffraction measurement can be made with the XYZ stage without removing the base from the first stage.

5. The diffractometer of claim 1 wherein the XYZ stage can be moved into a position where the rotation stage can be used to perform a measurement without removing the XYZ stage from the first stage.

6. An X-ray diffractometer comprising:
a base;
an X-ray source attached to the base;
a first stage that is attached to the base and rotates around an ω axis;
a second stage that is attached to the base and rotates around a 2θ axis;
an X-ray detector attached to the second stage;
a rotation stage that holds a crystal in a position suitable for a diffraction measurement and is mounted on the first stage at a first predetermined distance from the ω axis; and
an XYZ stage that holds large and multiple samples in a position suitable for a diffraction measurement and is mounted on the first stage at a position diametrically opposed to the rotation stage and at a second predetermined distance from the ω axis, both the rotation stage and the XYZ stage being mounted on the first stage during an X-ray diffraction measurement.

7. The diffractometer of claim 6 having an instrument center located along the ω axis and wherein the first and second predetermined distances are sufficiently large to allow a crystal mounted on the rotation stage to be positioned at the instrument center without interference from the XYZ stage and to allow a sample mounted on the XYZ stage to be positioned at the instrument center without interference from the rotation stage.

8. The diffractometer of claim 6 wherein the rotation stage comprises a base mounted on the first stage and a goniometer head rotating around a φ axis and removably attached to the base in a manner that the goniometer head can be removed and reattached to the base without re-aligning the diffractometer.

9. The diffractometer of claim 8 wherein the base is mounted on the first stage in a position where the goniometer head can be removed and a diffraction measurement can be made with the XYZ stage without removing the base from the first stage.

10. The diffractometer of claim 6 wherein the XYZ stage can be moved into a position where the rotation stage can be used to perform a measurement without removing the XYZ stage from the first stage.

11. A method for making X-ray diffraction measurements on an X-ray diffractometer having a rotation stage that holds a crystal in a position suitable for a diffraction measurement and an XYZ stage that holds large and multiple samples in a position suitable for a diffraction measurement both stages being mounted on a stage that rotates around an ω axis, the method comprising:
(a) moving the XYZ stage away from the ω axis without removing the XYZ stage from the stage that rotates around the ω axis;
(b) mounting a goniometer head that rotates around a φ axis on the rotation stage;
(c) mounting the crystal sample on the goniometer head and aligning the sample to an instrument center; and
(d) performing a single crystal X-ray diffraction measurement.

12. The method of claim 11 further comprising:
(e) removing the goniometer head from the rotation stage, leaving the rotation stage mounted on the stage that rotates around the ω axis;
(f) moving the XYZ stage towards the ω axis;
(g) mounting a sample on the XYZ stage and aligning the sample to the instrument center; and
(h) performing an X-ray diffraction measurement on the sample.

* * * * *